(12) United States Patent
Colin

(10) Patent No.: US 7,202,192 B2
(45) Date of Patent: *Apr. 10, 2007

(54) COMPOSITE CATALYSTS FOR THE DIRECT SYNTHESIS OF ALKYLHALOSILANES

(75) Inventor: Pascale Colin, Chassieu (FR)

(73) Assignee: Rhodia Chimie, Aubervilliers (FR)

( * ) Notice: Subject to any disclaimer, the term of this patent is extended or adjusted under 35 U.S.C. 154(b) by 5 days.

This patent is subject to a terminal disclaimer.

(21) Appl. No.: 11/148,204

(22) Filed: Jun. 9, 2005

(65) Prior Publication Data

US 2005/0283018 A1    Dec. 22, 2005

Related U.S. Application Data

(63) Continuation of application No. PCT/FR03/03612, filed on Dec. 8, 2003.

(51) Int. Cl.
*B01J 27/00* (2006.01)
*B01J 23/00* (2006.01)
*B01J 23/70* (2006.01)
*C07F 7/00* (2006.01)
*C07F 7/04* (2006.01)

(52) U.S. Cl. .................. 502/208; 502/344; 502/345; 502/352; 556/472; 556/473; 556/477

(58) Field of Classification Search ............... 502/208, 502/344, 345, 352; 556/472, 473, 477
See application file for complete search history.

(56) References Cited

U.S. PATENT DOCUMENTS

| | | | | |
|---|---|---|---|---|
| 4,656,301 A | * | 4/1987 | Prud'Homme et al. | 556/472 |
| 4,661,613 A | * | 4/1987 | Prud'Homme et al. | 556/472 |
| 4,762,940 A | * | 8/1988 | Halm et al. | 556/472 |
| 4,962,220 A | * | 10/1990 | Halm et al. | 556/473 |
| 4,966,986 A | * | 10/1990 | Halm et al. | 556/473 |
| 5,312,948 A | * | 5/1994 | Freeburne et al. | 556/472 |
| 5,596,119 A | * | 1/1997 | Halm et al. | 556/472 |

* cited by examiner

*Primary Examiner*—J. A. Lorengo
*Assistant Examiner*—Patricia L. Hailey
(74) *Attorney, Agent, or Firm*—Buchanan, Ingersoll & Rooney PC

(57) ABSTRACT

The alkylhalosilanes are directly synthesized by reacting an alkyl halide with silicon in the presence of a catalytically effective amount of (α) a copper metal or a copper-based compound catalyst and (β) a catalyst promoter intermixture therefor which comprises an effective minor amount of an additive β1 selected from the group consisting of tin, a tin-based compound and mixture thereof, an effective minor amount of an additive β2 selected from the group consisting of cesium, potassium and rubidium, and compound and mixture thereof, and an effective minor amount of an additive β3 selected from the group consisting of the element phosphorus, a phosphorus-based compound and mixture thereof.

34 Claims, No Drawings

COMPOSITE CATALYSTS FOR THE DIRECT SYNTHESIS OF ALKYLHALOSILANES

CROSS-REFERENCE TO PRIORITY/PCT APPLICATIONS

This application claims priority under 35 U.S.C. § 119 of FR 02/15528, filed Dec. 9, 2002, and is a continuation of PCT/FR 2003/003612, filed Dec. 8, 2003 and designating the U.S. (published in the French language on Jul. 29, 2004 as WO 2004/063205 A1; the title and abstract were also published in English), each hereby expressly incorporated by reference and each assigned to the assignee hereof.

CROSS-REFERENCE TO COMPANION APPLICATION

Copending application, U.S. patent Publication No. 2005/0283017, filed concurrently herewith and also assigned to the assignee hereof.

BACKGROUND OF THE INVENTION

1. Technical Field of the Invention

The present invention relates to a novel catalytic system and process for the direct synthesis of alkylhalosilanes catalyzed therewith.

2. Description of Background and/or Related and/or Prior Art

The industrial process for the manufacture of alkylhalosilanes and, for example, of dimethyldichlorosilane, subsequently referred to as DMDCS, is a well known process which is disclosed in particular in U.S. Pat. No. 2,380,995 and in the text by Walter Noll, *Chemistry and Technology of Silicones*, 1968, published by Academic Press Inc., London, pages 26–41.

According to this "direct synthesis" or "Rochow synthesis" process, the alkylhalosilanes, for example DMDCS, are manufactured directly by reaction of methyl chloride with a solid contact body formed of silicon and of a catalyst comprising copper, according to the reaction:

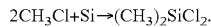

$$2CH_3Cl + Si \rightarrow (CH_3)_2SiCl_2.$$

In reality, other coproducts, such as those indicated below, are formed during the direct synthesis: other alkylhalosilanes, such as methyltrichlorosilane $CH_3SiCl_3$, subsequently referred to as MTCS, and trimethylchlorosilane $(CH_3)_3SiCl$, subsequently referred to as TMCS; halogenated alkylhydrosilanes, such as, for example, methylhydrodichlorosilane $(CH_3)HSiCl_2$, subsequently referred to as MHDCS; and heavy products which are polysilanes and in particular disilanes, such as, for example, trimethyltrichlorodisilane $(CH_3)_3Si_2Cl_3$ and dimethyltetrachlorodisilane $(CH_3)_2Si_2Cl_4$.

Among all the products obtained by direct synthesis, the dialkyldihalosilane, and for example DMDCS, is the main product, that is to say the product obtained in predominant amount. This product is highly desirable as, after hydrolysis and polymerization, it makes it possible to obtain oils and gums which are base products for the manufacture of silicones.

It is known to use copper, whether in the form of copper metal or in the form of copper-based chemical compounds, as catalyst of the direct synthesis reaction.

In order, in particular:

to improve the mean activity (also referred to as productivity) of the contact body comprising the combination based on silicon and on catalyst, this activity (or productivity) being evaluated as weight of the silanes obtained per hour and per kilogram of silicon initially involved, to also improve the selectivity for the dialkyldihalosilane, and for example for DMDCS, evaluated, for example, by the mean mol % of DMDCS with respect to all the silanes obtained and by the MTCS/DMDCS mean ratio by weight, and to lower the content by weight of "heavy" products with respect to the silanes obtained, it has to date been proposed to add, to the copper, a promoter combination comprising one or more promoting additive(s). These additives can be: zinc or a zinc halide (U.S. Pat. No. 2,464,033), aluminum (U.S. Pat. Nos. 2,403,370 and 2,427,605), tin, manganese, nickel and silver (GB-A-1,207,466), cobalt (GB-A-907,161), potassium chloride (SU-A-307,650), or arsenic or an arsenic compound (U.S. Pat. No. 4,762,940).

EP-A-0-138,678 and EP-A-0-138,679 describe the use of a copper catalyst as a mixture with an improved promoter combination which includes:

30 to 1000 ppm (calculated as weight of metal with respect to the weight of silicon involved) of at least one metal selected from among tin and antimony or of a compound based on tin and/or on antimony, optionally 0.1 to 3% (calculated as indicated above) of zinc metal or of a zinc-based compound, and in the case of EP-A-0-138,678:0.05 to 4% (calculated as indicated above) of cesium or of a cesium compound, taken alone or as a mixture with at least one other alkali metal selected from among lithium, sodium, potassium, rubidium and a compound based on said alkali metal; or, in the case of EP-A-0-138,679:0.05 to 2% (calculated as indicated above) of at least one alkali metal selected from among lithium, sodium, potassium, rubidium and a compound based on said same alkali metal.

U.S. Pat. No. 4,601,101 describes the use of a copper catalyst as a mixture with another improved promoter combination which includes:

5 to 200 ppm (calculated as weight of metal with respect to the weight of silicon involved) of tin or of a tin-based compound, optionally 100 to 10,000 ppm (calculated as indicated above) of zinc metal or of a zinc-based compound, and 25 to 931 ppm (calculated as indicated above) of elemental phosphorus, of a metal phosphide and/or of a compound capable of providing a metal phosphide in the reaction body of the direct synthesis.

However, despite the importance of the catalytic systems (copper catalyst as a mixture with a promoter combination) provided in the abovementioned prior art, research continues in this field in order to obtain better performances than those obtained with the best catalytic systems known previously, in particular the following systems: Cu+optionally Zn+Sn+Cs and Cu+optionally Zn+Sn+P.

SUMMARY OF THE INVENTION

The present invention provides a process and a novel catalytic system for conducting the direct synthesis process which is different from the best catalytic systems referred to above, in particular in that the promoter combination does not comprise zinc or a zinc-based compound, and which makes it possible to obtain, in particular, a mean activity, a selectivity for dialkyldihalosilane and a content by weight of heavy byproducts which exhibit more advantageous values than those recorded with the best catalytic systems known previously, comprising or not comprising zinc in the promoter combination.

This result is achieved by the present invention. More specifically, the present invention features a process for the preparation of alkylhalosilanes by reaction of an alkyl halide, preferably $CH_3Cl$, with a solid body, referred to as contact body, formed of silicon and of a catalytic system comprising (α) copper metal or a copper-based compound and (β) a promoter combination comprising 10 to 500 ppm (calculated as weight of metal with respect to the weight of silicon involved) of an additive β1 selected from among tin, a tin-based compound and a mixture of these entities, said process being characterized in that the promoter combination (β) additionally comprises:

0.01 to 2% (calculated as weight of metal with respect to the weight of silicon involved) of an additive β2 selected from among cesium, potassium and rubidium, a compound based on said alkali metal and a mixture of these entities, and 50 to 3,000 ppm (calculated as weight of elemental phosphorus with respect to the weight of silicon involved) of an additive β3 selected from among the element phosphorus, a phosphorus-based compound and a mixture of these entities.

DETAILED DESCRIPTION OF BEST MODE AND SPECIFIC/PREFERRED EMBODIMENTS OF THE INVENTION

The catalyst (α) is advantageously employed at a content by weight ranging from 1 to 20%, preferably ranging from 2 to 12%, with respect to the weight of silicon involved.

Use may be made, in place of copper metal, of a copper compound, in particular of: a copper halide, such as, for example, cuprous chloride or cupric chloride; a copper carboxylate, such as, for example, cuprous formate, cupric formate, cuprous acetate or cupric acetate; or a copper oxide, such as, for example, $Cu_2O$ or $CuO$.

It has been demonstrated, in accordance with the present invention, that better results, in particular for selectivity and for degree of conversion of the silicon, are obtained if the copper is introduced in the form of copper metal and/or in the form of cuprous chloride.

The content by weight of tin and/or of tin compound (promoting additive β1, the content of which is calculated as weight of tin metal) advantageously ranges from 10 to 500 ppm and preferably from 30 to 300 ppm, with respect to the weight of silicon involved.

It is necessary to have at least 10 ppm of tin metal. This is because it has been found in accordance with the invention that the beneficial effects of the promoting additives β2 based on an alkali metal and/or on a compound of an alkali metal and β3 based on phosphorus are only obtained in the presence of tin and/or of a tin compound. In addition, a content by weight of greater than 500 ppm would have a harmful effect on the reaction and in particular on the selectivity.

Use is made, as tin-based compound, for example, of tin chloride. The promoting additive β1 which is preferably used is tin metal; advantageously, this tin metal can be added in the form of bronze.

The content by weight of alkali metal and/or of alkali metal compound (promoting additive β2, the content of which is calculated as alkali metal) advantageously ranges from 0.01 to 2% by weight and preferably from 0.05 to 1.0% by weight. Below 0.01% by weight, the action of the alkali metal is not really detectable and, above 2% by weight, the alkali metal does not have the expected effect on the selectivity.

Use may be made, as compound of an alkali metal selected from among Cs, K and Rb, of: halides, and for example the chloride; or carboxylates, and for example the formate or the acetate. Cesium chloride, potassium chloride, rubidium chloride and/or a mixture of these compounds are the promoting additives β2 which are preferably used.

The content by weight of elemental phosphorus and/or of compound based on phosphorus (promoting additive β3, the content of which is calculated as weight of elemental phosphorus) advantageously ranges from 50 to 3,000 ppm and preferably from 80 to 1,500 ppm and more preferably still from 90 to 800 ppm. Below 50 ppm, the action of the phosphorus is not really detectable and, above 3,000 ppm, the phosphorus has a poisonous effect which reduces the selectivity.

The phosphorus which is used in the present invention as promoting additive can be elemental phosphorus, such as, for example, red phosphorus, white phosphorus and black phosphorus. Use may be made, as phosphorus-based compound, of: metal phosphides, and for example aluminum phosphide, calcium phosphide $Ca_3P_2$, copper phosphide $Cu_3P$, nickel phosphide $NiP_2$, tin phosphide $SnP$, the iron phosphides $FeP$, $Fe_2P$ and $Fe_3P$, the zinc phosphides $Zn_3P_2$ and $ZnP_2$, or silicon phosphide; or phosphorus-based compounds capable of forming metal phosphides of the type of those mentioned above during the direct synthesis reaction between the alkyl halide and the contact body based on silicon and on the catalytic system (α)+(β). Use may also be made, as other phosphorus-based compounds, of certain alloys which are known to comprise both phosphorus and a metal part and which are readily available commercially, for example the copper-phosphorus alloys which comprise approximately from 7 to 15% by weight of phosphorus. Copper phosphide $Cu_3P$ and the copper-phosphorus alloys are the promoting additives β3 which are preferably used.

More preferably, the amounts of the additives β2 and β3 are selected within the abovementioned regions of general and preferred variation so that the ratio:

$$\frac{\text{number of gram atoms of alkali metal}}{\text{number of gram atoms of elemental phosphorus}}$$

varies from 1 to 20, preferably from 1.2 to 15 and more preferably still from 1.5 to 12.

Also, it is desirable for the particle size of the silicon to be such that the mean diameter of at least 50% by weight of the particles ranges from 10 to 500 μm and preferably from 60 to 200 μm. Likewise, the catalyst (α) and the group of promoters (β) are also advantageously in the form of particles, the mean diameter of at least 50% by weight of the particles advantageously ranging from 1 to 100 μm.

The direct synthesis process according to the invention can generally be carried out in one of the three following types of apparatus: a reactor of the stirred bed type, such as that described in U.S. Pat. No. 2,449,821, a reactor of the fluidized bed type, such as that described in U.S. Pat. No. 2,389,931, or a rotary kiln.

The constituent ingredients of the catalytic system (α)+(β) can also be used deposited on a particulate inorganic material, such as sand, ground silica, silica gel, alumina, ground refractory brick, catalysts for the cracking of oil, zeolites and calcined clays, as described in FR-A-1-545,407.

The direct synthesis reaction advantageously is carried out at a temperature ranging from 280 to 400° C. and preferably from 300 to 380° C. It can be carried out, in total or in part, under an absolute pressure of alkyl halide equal to atmospheric pressure (1 bar) or greater than atmospheric pressure; when the latter case prevails, the reaction is generally carried out under an absolute pressure ranging from 1.1 to 8 bar and preferably ranging from 1.5 to 4 bar.

In order to carry out the direct synthesis reaction, an initial stage of activation of the contact body (formed by the combination based on silicon+catalyst+promoters) is advantageously performed beforehand, as is well known; one of the activation means which is highly suitable can entail heating said contact body to a certain temperature which can be, by a few degrees to several tens of degrees, less than or greater than the temperature selected for the direct synthesis reaction and which is within the general or preferred range mentioned above.

On using the catalytic system $(\alpha)+(\beta)$ according to the invention, it is possible to obtain, when the reaction is carried out, both in a stirred bed and in a fluidized bed, at a temperature ranging from 280° C. to 400° C. and preferably ranging from 300 to 380° C., a high mean activity, a high selectivity for dialkyldihalosilane and a low content by weight of heavy byproducts.

As regards the mean activity of the catalytic system, it is, for example, on the order of or greater than 330 g of silanes/h/kg of Si, being able to reach 370 g of silanes/h/kg of Si and more.

As regards the selectivity, evaluated, for example, by the mean mol % of DMDCS with respect to all the silanes obtained and by the MTCS/DMDCS mean ratio by weight:
  mean mol % of DMDCS: the value obtained is on the order of or greater than 90%, being able to reach 93% and more,
  MTCS/DMDCS mean ratio by weight: the value obtained is on the order of or less than 0.05, being able to reach 0.035.

As regards the percentage of heavy products formed with respect to the silanes obtained, it can be as low as 1.2% by weight and it is generally less than 23% by weight.

The values obtained as regards in particular mean activity, selectivity for dialkyldihalosilane and content by weight of heavy byproducts, in the proportions such as those mentioned above, appear as particularly surprising with regard to the teachings of the prior art, which have remained completely silent to date on the values which it is possible to obtain by using the catalytic systems of the direct synthesis process in accordance with this prior art not comprising a zinc-based promoter.

In order to further illustrate the present invention and the advantages thereof, the following specific examples are given, it being understood that same are intended only as illustrative and in nowise limitative. In said examples to follow, all parts and percentages are given by weight, unless otherwise indicated.

In the following examples, unless otherwise mentioned, use is made of a cylindrical pilot-scale reactor with an internal diameter of 60 mm and a height of 250 mm equipped at its base with a sparger made of sintered glass. The silicon and the catalytic system are charged in the form of a powder, the mean size of at least 50% by weight of the particles of which ranges from 60 to 200 µm.

The reaction is carried out in a stirred bed and the reactor is equipped with an external heating element.

EXAMPLES

Example 1

Catalytic System: Cu/Sn/Cs/P (1029 ppm):

A powder of 210 g of silicon, 16.4 g of CuCl, 0.38 g of bronze comprising 10% by weight of tin, and 1.9 g of CsCl is charged to a cylindrical vertical glass reactor equipped with a metal stirrer and with a sparger made of sintered glass. After initiating the reaction and when the performance has stabilized (i.e. after reacting for 4 hours), 3 g of $Cu_3P$ comprising 7.2% by weight of phosphorus are added.

The reactor is gradually heated to 200° C. under a stream of nitrogen. Then, while continuing to raise the temperature of the reactor, the nitrogen tap is closed and the introduction is begun of the methyl chloride with a flow rate, measured at 20° C., of 60 g/h.

The temperature of the reactor is regulated at 360° C. and the methyl chloride flow rate is maintained at 60 g/h. The reaction is halted by the operator after maintaining at 360° C. for 4 hours in order to allow the addition of $Cu_3P$ when the reactor has reached ambient temperature. Once the addition has been carried out, the rise in temperature and the introduction of $CH_3Cl$ are controlled as above.

The test takes place at atmospheric pressure. The test is halted by the operator after producing methylchlorosilanes (MCSs) for 8 hours.

This test produced silanes with a mean productivity or activity of 335 g of silanes per hour and per kg of Si initially charged to the reactor.

The mixture produced is analyzed by gas chromatography and it is characterized by a mean mol % of DMDCS of 93.3%.

The MTCS/DMDCS ratio obtained is equal to 0.037 (% by weight/% by weight).

The proportion of "heavy" products (polysilanes) obtained amounts to 1.7% by weight.

Example 2

Catalytic System: Cu/Sn/Cs/P (103 ppm):

A powder of 210 g of silicon, 16.4 g of CuCl, 0.38 g of bronze comprising 10% by weight of tin, and 1.9 g of CsCl is charged to a cylindrical vertical glass reactor equipped with a metal stirrer and with a sparger made of sintered glass. After initiating the reaction and when the performance has stabilized (i.e., after reacting for 3 hours, 30 minutes), 0.275 g of $Cu_3P$ comprising 7.2% by weight of phosphorus is added.

The reactor is gradually heated to 200° C. under a stream of nitrogen. Then, while continuing to raise the temperature of the reactor, the nitrogen tap is closed and the introduction is begun of the methyl chloride with a flow rate, measured at 20° C., of 60 g/h.

The temperature of the reactor is regulated at 360° C. and the methyl chloride flow rate is maintained at 60 g/h. The reaction is halted by the operator after maintaining at 360° C. for 3 hours, 30 minutes in order to allow the addition of $Cu_3P$ when the reactor has reached ambient temperature. Once the addition has been carried out, the rise in temperature and the introduction of $CH_3Cl$ are controlled as above. The pressure of the test is regulated at 3.5 bar absolute. The test is halted by the operator after producing MCS for 8 hours.

This test produced silanes with a mean productivity or activity of 380 g of silanes per hour and per kg of Si initially charged to the reactor.

The mixture produced is analyzed by gas chromatography and it is characterized by a mean mol % of DMDCS of 94.1%.

The MTCS/DMDCS ratio obtained is equal to 0.035 (% by weight/% by weight).

The proportion of "heavy" products (polysilanes) obtained amounts to 1.2% by weight.

Comparative Tests

Test A:

Catalytic System: Cu/Zn/Sn:

A powder of 210 g of silicon, 16.4 g of CuCl, 1.64 g of $ZnCl_2$ and 0.38 g of bronze comprising 10% by weight of tin is charged to a cylindrical vertical glass reactor equipped with a metal stirrer and with a sparger made of sintered glass.

The reactor is gradually heated to 200° C. under a stream of nitrogen. Then, while continuing to raise the temperature of the reactor, the nitrogen tap is closed and the introduction is begun of methyl chloride with a flow rate, measured at 20° C., of 60 g/h.

The temperature of the reactor is regulated at 360° C. and the methyl chloride flow rate is maintained at 60 g/h for 8 hours; the test takes place at atmospheric pressure.

This test produced silanes with a mean productivity or activity of 326 g of silanes per hour and per kg of Si initially charged to the reactor.

The mixture produced is analyzed by gas chromatography and it is characterized by a mean mol % of DMDCS of 86.8%.

The MTCS/DMDCS ratio obtained is equal to 0.074 (% by weight/% by weight).

The proportion of "heavy" products (polysilanes) obtained amounts to 3.7% by weight.

Test B:

Catalytic System: Cu/Sn/Cs:

A powder of 210 g of silicon, 16.4 g of CuCl, 0.38 g of bronze comprising 10% by weight of tin, and 1.9 g of CsCl is charged to a cylindrical vertical glass reactor equipped with a metal stirrer and with a sparger made of sintered glass.

The reactor is gradually heated to 200° C. under a stream of nitrogen. Then, while continuing to raise the temperature of the reactor, the nitrogen tap is closed and the introduction is begun of the methyl chloride with a flow rate, measured at 20° C., of 60 g/h.

The temperature of the reactor is regulated at 360° C. and the methyl chloride flow rate is maintained at 60 g/h for 8 hours; the test takes place at atmospheric pressure.

This test produced silanes with a mean productivity or activity of 302 g of silanes per hour and per kg of Si initially charged to the reactor.

The mixture produced is analyzed by gas chromatography and it is characterized by a mean mol % of DMDCS of 92.4%.

The MTCS/DMDCS ratio obtained is equal to 0.040 (% by weight/% by weight).

The proportion of "heavy" products (polysilanes) obtained amounts to 2.3% by weight.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the direct synthesis of alkylhalosilanes, comprising reacting an alkyl halide with silicon in the presence of a catalytically effective amount of (α) a copper metal or a copper-based compound catalyst and (β) a catalyst promoter intermixture therefor which comprises an effective minor amount of an additive β1 selected from the group consisting of tin, a tin-based compound and mixture thereof, an effective minor amount of an additive β2 selected from the group consisting of cesium, potassium and rubidium, and compound and mixture thereof, and an effective minor amount of an additive β3 selected from the group consisting of the element phosphorus, a phosphorus-based compound and mixture thereof: wherein the additives β2 and β3 are present in such amounts that the ratio:

$$\frac{\text{number of gram atoms of alkali metal}}{\text{number of gram atoms of elemental phosphorus}}$$

ranges from 1 to 20.

2. The process as defined by claim 1, said catalyst promoter intermixture comprising from 10 to 500 ppm of additive β1, from 0.01% to 2% of additive β2 and from 50 to 3,000 ppm of additive β3, each by weight with respect to the weight of the silicon.

3. The process as defined by claim 2, said catalyst promoter intermixture comprising from 30 to 300 ppm of additive β1.

4. The process as defined by claim 2, said catalyst promoter intermixture comprising from 0.05% to 1.0% of additive β2.

5. The process as defined by claim 2, said catalyst promoter intermixture comprising from 80 to 1,500 ppm of additive β3.

6. The process as defined by claim 1, said additive β1 comprising tin metal.

7. The process as defined by claim 6, said additive β1 comprising bronze.

8. The process as defined by claim 1, said additive β2 comprising cesium chloride, potassium chloride, rubidium chloride and/or mixture thereof.

9. The process as defined by claim 1, said additive β3 comprising copper phosphide $Cu_3P$ and/or a copper-phosphorus alloy.

10. The process as defined by claim 1, said ratio ranging from 1.2 to 15.

11. The process as defined by claim 1, said ratio ranging from 1.5 to 12.

12. The process as defined by claim 1, comprising from 1% to 20% by weight of said catalyst (α), with respect to the weight of the silicon.

13. The process as defined by claim 1, said catalyst (α) comprising copper metal, cuprous chloride and/or mixture thereof.

14. The process as defined by claim 1, carried out at a temperature ranging from 280° C. to 400° C.

15. The process as defined by claim 1, said catalyst (α) and catalyst promoter intermixture (β) being devoid of zinc values.

16. The process as defined by claim 1, the silicon comprising particulates thereof, the mean diameter of at least 50% by weight of said particles ranging from 10 to 500 μm.

17. The process as defined by claim 16, the catalyst (α) and catalyst promoter intermixture (β) also comprising particulates thereof, the mean diameter of at least 50% by weight of said particles ranging from 1 to 100 μm.

18. The process as defined by claim 17, said particulate catalyst (α) and catalyst promoter intermixture (β) being deposited onto a particulate inorganic support therefor.

19. The process as defined by claim 1, the mean mol % of DMDCS produced relative to the total amount of silanes produced being at least 90%.

20. The process as defined by claim 1, the mean ratio by weight of MTCS/DMDCS produced being no greater than 0.05.

21. The process as defined by claim 1, said alkyl halide comprising methyl chloride.

22. A composite catalyst system suited for catalyzing the direct synthesis of alkylhalosilanes, comprising a catalytically effective amount of (α) a copper metal or a copper-based compound catalyst and (β) a catalyst promoter intermixture therefor which comprises an effective minor amount of an additive β1 selected from the group consisting of tin, a tin-based compound and mixture thereof, an effective minor amount of an additive β2 selected from the group consisting of cesium, potassium and rubidium, and compound and mixture thereof, and an effective minor amount of an additive β3 selected from the group consisting of the element phosphorus, a phosphorus-based compound and mixture wherein the additives β2 and β3 are present in such amounts that the ratio:

$$\frac{\text{number of gram atoms of alkali metal}}{\text{number of gram atoms of elemental phosphorus}}$$

ranges from 1 to 20.

23. The composite catalyst system as defined by claim 22, said catalyst promoter intermixture comprising from 10 to 500 ppm of additive β1, from 0.01% to 2% of additive β2 and from 50 to 3,000 ppm of additive β3, each by weight with respect to the weight of the silicon.

24. The composite catalyst system as defined by claim 23, said catalyst promoter intermixture comprising from 30 to 300 ppm of additive β1.

25. The composite catalyst system as defined by claim 23, said catalyst promoter intermixture comprising from 0.05% to 1.0% of additive β2.

26. The composite catalyst system as defined by claim 23, said catalyst promoter intermixture comprising from 80 to 1,500 ppm of additive β3.

27. The composite catalyst system as defined by claim 22, said additive α1 comprising tin metal.

28. The composite catalyst system as defined by claim 27, said additive β1 comprising bronze.

29. The composite catalyst system as defined by claim 22, said additive β2 comprising cesium chloride, potassium chloride, rubidium chloride and/or mixture thereof.

30. The composite catalyst system as defined by claim 22, said additive β3 comprising copper phosphide $Cu_3P$ and/or a copper-phosphorus alloy.

31. The composite catalyst system as defined by claim 22, said catalyst (α) comprising copper metal, cuprous chloride and/or mixture thereof.

32. The composite catalyst system as defined by claim 22, said catalyst (α) and catalyst promoter intermixture (β) being devoid of zinc values.

33. The composite catalyst system as defined by claim 22, the catalyst (α) and catalyst promoter intermixture (β) comprising particulates thereof, the mean diameter of at least 50% by weight of said particles ranging from 1 to 100 μm.

34. The composite catalyst system as defined by claim 33, said particulate catalyst (α) and catalyst promoter intermixture (β) being deposited onto a particulate inorganic support therefor.

* * * * *